(12) United States Patent
Desai et al.

(10) Patent No.: US 12,048,595 B2
(45) Date of Patent: Jul. 30, 2024

(54) SURGICAL APPARATUS AND METHOD

(71) Applicant: EUREKA INVENTIONS LIMITED, Newcastle (GB)

(72) Inventors: Aditi Kiran Desai, Wolverhampton (GB); Kiran Kamlakant Desai, Wolverhampton (GB)

(73) Assignee: EUREKA INVENTIONS LIMITED, Newcastle (GB)

( * ) Notice: Subject to any disclaimer, the term of this patent is extended or adjusted under 35 U.S.C. 154(b) by 630 days.

(21) Appl. No.: 17/287,762

(22) PCT Filed: Oct. 25, 2019

(86) PCT No.: PCT/GB2019/053030
§ 371 (c)(1),
(2) Date: Apr. 22, 2021

(87) PCT Pub. No.: WO2020/084313
PCT Pub. Date: Apr. 30, 2020

(65) Prior Publication Data
US 2021/0378780 A1    Dec. 9, 2021

(30) Foreign Application Priority Data

Oct. 26, 2018 (GB) .................................. 1817455
Mar. 26, 2019 (GB) .................................. 1904133

(51) Int. Cl.
*A61B 90/00* (2016.01)
*A61B 50/20* (2016.01)
(Continued)

(52) U.S. Cl.
CPC .............. *A61B 90/08* (2016.02); *A61B 50/20* (2016.02); *A61F 13/44* (2013.01);
(Continued)

(58) Field of Classification Search
CPC ......... A61B 90/08; A61B 50/20; A61B 90/90; A61B 2090/0805; A61B 50/37;
(Continued)

(56) References Cited

U.S. PATENT DOCUMENTS 2,474,157 A * 6/1949 Needlman .......... G08B 13/1472
340/568.8
3,630,202 A    12/1971 Small
(Continued)

FOREIGN PATENT DOCUMENTS

CN    106604687 A    4/2017
WO    2013009957 A1   1/2013

OTHER PUBLICATIONS

International Search Report issued in PCT/GB2019/053030 dated Jan. 9, 2020, pp. 1-5.

*Primary Examiner* — Eric Blount
(74) *Attorney, Agent, or Firm* — ARENTFOX SCHIFF LLP

(57) ABSTRACT

A surgical apparatus including a body having at least one port; and at least one item of surgical equipment; in which each item of surgical equipment includes an engagement member arranged to engage a port of the body, and in which the apparatus further includes a control circuit for determining for each port whether the engagement member of one of the items of surgical equipment is engaged to the port; and an indicator controlled by the control circuit and arranged to indicate whether each engagement member is engaged with the at least one port.

19 Claims, 9 Drawing Sheets

(51) Int. Cl.
*A61F 13/44* (2006.01)
*A61B 17/00* (2006.01)

(52) U.S. Cl.
CPC .............. *A61B 2017/00119* (2013.01); *A61B 2090/0805* (2016.02); *A61B 2090/0806* (2016.02)

(58) Field of Classification Search
CPC .......... A61B 90/39; A61B 2017/00199; A61B 2050/0056; A61B 2050/0065; A61B 46/00; A61B 5/742; A61B 5/746; A61B 50/10; A61B 50/13; A61B 50/30; A61B 50/36; A61B 90/37; A61B 90/98; A61B 2090/0804; A61B 2090/3966; A61B 2017/00119; A61B 2017/00734; A61B 2050/375; A61B 2090/0806; A61B 2090/376; A61B 90/36; A61B 90/00; A61B 2090/3987; A61B 2090/3991; A61B 1/00165; A61B 1/00179; A61B 1/0623; A61B 1/07; A61B 1/24; A61B 2090/3908; A61F 13/44; A61F 13/36; A61F 2013/8497; A61F 2013/8414
See application file for complete search history.

(56) References Cited

U.S. PATENT DOCUMENTS

| | | | | |
|---|---|---|---|---|
| 3,644,927 A * | 2/1972 | Green | ................. | G08B 26/005 |
| | | | | 307/413 |
| 3,948,390 A | 4/1976 | Ferreri | | |
| 4,042,918 A * | 8/1977 | Klitzman | ............... | A63B 55/40 |
| | | | | 206/315.6 |
| 4,317,112 A | 2/1982 | Beier et al. | | |
| 4,514,172 A | 4/1985 | Behringer | | |
| 5,664,582 A * | 9/1997 | Szymaitis | ................ | A61B 5/06 |
| | | | | 128/897 |
| 6,026,818 A | 2/2000 | Blair et al. | | |
| 7,180,014 B2 * | 2/2007 | Farber | .................... | G16H 40/20 |
| | | | | 606/1 |
| 7,297,834 B1 * | 11/2007 | Shapiro | ................... | A61F 13/44 |
| | | | | 604/362 |
| 9,089,366 B2 * | 7/2015 | Garner-Richards | ... | A61B 90/90 |
| 9,168,104 B2 * | 10/2015 | Dein | ................ | A61B 50/362 |
| 11,045,274 B2 * | 6/2021 | Dachs, II | ............... | A61B 90/98 |
| 11,678,952 B2 * | 6/2023 | Stewart | ................... | A61F 13/44 |
| | | | | 340/572.4 |
| 11,793,591 B2 * | 10/2023 | Fleck | ................. | G06K 7/10316 |
| 2006/0255938 A1 | 11/2006 | Van den Brink | | |
| 2010/0179822 A1 * | 7/2010 | Reppas | ................ | G06Q 10/087 |
| | | | | 705/2 |
| 2013/0079590 A1 * | 3/2013 | Bengtson | .......... | A61F 13/15268 |
| | | | | 604/93.01 |
| 2015/0245955 A1 * | 9/2015 | Choudhury | ........... | A61F 15/001 |
| | | | | 604/362 |
| 2015/0305735 A1 | 10/2015 | Gorek et al. | | |
| 2019/0000589 A1 * | 1/2019 | Vanderwoude | ......... | A61F 13/44 |
| 2023/0165657 A1 * | 6/2023 | Fleck | ..................... | A61F 13/36 |
| | | | | 340/8.1 |

* cited by examiner

SURGICAL APPARATUS AND METHOD

CROSS-REFERENCE TO RELATED APPLICATIONS

This application is a U.S. National Stage entry under 35 U.S.C. § 371 based on International Application No. PCT/GB2019/053030, filed on Oct. 25, 2019, which claims priority to GB Patent Application Nos. 1817455.7, filed on Oct. 26, 2018 and 1904133.4, filed on Mar. 26, 2019. The embodiment of the priority applications are hereby incorporated herein in their entirety by reference.

TECHNICAL FIELD OF THE INVENTION

This invention relates to a surgical apparatus and associated method.

BACKGROUND

The problem of retained foreign objects after surgery is well known. Such events amount to around a third of "never events" for the British National Health Service—events that through careful management should never happen, but due to human factors still unfortunately do. Retaining a foreign object—such as a surgical swab or sponge—inside a patient after surgery can have catastrophic implications for patients, health care professionals and healthcare provider organisations.

Whilst most surgeons and those who assist have been rigorously trained in meticulous counting in and counting out of surgical items, errors still occur, particularly as such processes are heavily dependent on human factors, in what can be a stressful and unpredictable environment. Whilst specialised counting trays, such as that disclosed in US Patent Application publication US2016/0262843, can help, they are still subject to human error.

In the three years up to 2018, in England alone there were 164 surgical swabs (otherwise known as surgical sponges) retained in patients. Medicolegal and compensation costs averaged £59,000 per patient (ranging from £23,000 to £1,456,000; all figures are in pounds sterling). The number of claims from the years 2000/2001 to 2016/2017 is 2008, with the sum of damages being about £81 million.

Prior art attempts to solve this problem using technical means have included including radio frequency identification (RFID) tags in all such items, and then scanning the patient for such tags before closing up any incisions in the patient (as described in US Patent Application publication US2008/0051746). However, the scanners are bulky and expensive, as is including a tag in each surgical item. Furthermore, the patient's body may act to block the signals from such tags if the items are, as they are intended to be used during surgery, placed within a user's body.

Another prior art attempt to solve this problem (described in U.S. Pat. No. 5,931,824) uses barcodes on each surgical item, and a barcode scanner to scan items into and out of the patient's body. However, the scanners are inconveniently bulky and expensive, and blood and other bodily fluids can smear the barcodes, making them tricky to read.

SUMMARY OF THE INVENTION

As such, it would be desirable to avoid at least some of problems identified above with respect to the prior art.

According to a first aspect of the invention, we provide a surgical apparatus comprising:
  a body having at least one ports; and
  at least one of item of surgical equipment;
  in which each of the items of surgical equipment comprises an engagement member arranged to engage a port of the body, and in which the apparatus further comprises:
    a control circuit arranged to determine for each port whether the engagement member of one of the items of surgical equipment is engaged to the port; and
    an indicator controlled by the control circuit and arranged to indicate whether the engagement members are engaged with the at least one port.

Typically, the body will have a plurality of ports, and there will be a plurality of items of surgical equipment.

As such, the body can indicate whether all of the items of surgical equipment have been engaged with the body and as such are no longer within the body of a patient. There is much less reliance on human errors. The engagement members can be relatively simple, and do not need to carry any readable data or transmit any data to a separate location.

Typically, the indicator may comprise a visual indicator such as a light emitting indicator. This may illuminate only when (or only when not) all of the engagement members are engaged with the ports.

The indicator may additionally or alternatively comprise an audible indicator, such as a sound generating apparatus (such as a buzzer or other sounder) which is arranged to generate a noise when not all of (or when all of) the engagement members are engaged with the ports. Typically, the sound generating apparatus may be arranged to generate a sound at repeated intervals; typically, the interval may be between 5 seconds and 5 minutes; typically, the interval will be between 2 and 4 minutes.

The indicator may be a mechanical indicator which moves between at least two different states (e.g. different colours) depending on whether each engagement member engages the respective port. As such, the control circuit may comprise a mechanical mechanism which moves the mechanical indicator between its states.

The items of surgical equipment may comprise or consist of items taken from one or more of the following groups:
  surgical swabs/sponges;
  throat packs;
  surgical vaginal tampons;
  surgical tools, including retractors and scalpels.

At least one, or potentially all, of the items of surgical equipment may be provided with an elongate tail typically carrying the engagement member at one end and connected to a body of the item at another end. Typically, each tail may be at least 5 cm, preferably at least 7.5 cm long. This allows for more convenient connection to the body, especially after surgery when the body of each item may be carrying or containing bodily fluids such as blood. The tail may comprise a radio-opaque filament, such as a metallic wire, to aid with locating the item using x-rays or the like. The tail may be provided with a loop adjacent to the engagement member; surgeons or those assisting them can attach clamps to such loops to aid location and removal of the surgical item.

The control circuit and/or the indicator may be provided within the body. Typically, the body will comprise a power source, such as a battery, arranged to power the control circuit and/or the indicator.

Each port may comprise a socket in which at least one of the engagement members may be received; as such, each engagement member may comprise a plug sized and shaped to fit within the socket of a port (although the converse may be true). Typically, the control circuit will be arranged to determine whether the plug of each item or surgical equipment has been received within the socket of each port. Alternatively, each port may comprise a groove in which the engagement member can be received; typically, the engagement member may comprise the tail of an item of surgical equipment. The control circuit may comprise a light source and a light sensor for each groove, wherein the control circuit is arranged to determine that an item of surgical equipment is engaged in the port if light from the light source is blocked by the engagement member and does not reach the light sensor.

The control circuit may comprise transmission means arranged to transmit the status of the engagement of the engagement members in the ports to a remote location. This may aid in remote monitoring of the surgery, and in providing an audit trail.

In one embodiment, the body may be worn on the patient's body, typically as a wristband. The body or the engagement member may comprise a signalling circuit which signals to an external alarm circuit that the item of surgical equipment is still within the patient. The signalling circuit may be deactivated when the engagement member engages a port of the body. As such, if the external alarm circuit is positioned at an exit of a hospital, clinic or ward, patients can be stopped from leaving if they are still carrying an item of surgical equipment.

According to a second aspect of the invention, we provide a surgical apparatus comprising:
 a body having a plurality of ports; and
 a plurality of items of surgical equipment;
in which each of the items of surgical equipment comprises an engagement member arranged to engage one of the ports, and in which the apparatus further comprises:
 a control circuit arranged to determine for each port whether the engagement member of one of the items of surgical equipment is engaged to the port; and
 an indicator controlled by the control circuit and arranged to indicate whether the engagement members are engaged with the ports.

The surgical apparatus may have any of the optional features of the first aspect of the invention.

According to a third aspect of the invention, there is provided a method of surgery using the apparatus of the first or second aspects of the invention, comprising:
 providing the plurality of items of surgical equipment (or each item of surgical equipment) with the engagement member of each item connected to one of the ports of the body;
 detaching the engagement member(s) from the port(s) in order to use the items in surgery;
 using the item(s) of surgical equipment in surgery on a patient;
 after the usage of each item of surgical equipment, engaging the engagement member to a port of the body;
 before the surgery has finished, checking that the indicator indicates that all of the (or each) engagement member (s) have been engaged with the ports.

Thus, this method ensures that all of the items of surgical equipment have been removed from the patient and are engaged with the body.

The method of surgery of the second aspect of the invention can include, and the surgical apparatus can be used in, any surgical operation, including medical interventions in the human body which do not involve incisions or cutting into the body, such as during childbirth or in simple installation of a throat pack without any further surgical intervention.

BRIEF DESCRIPTION OF THE DRAWINGS

There now follows, by way of example only description of embodiments of the present invention, described with reference to the accompanying drawings, in which.

DETAILED DESCRIPTION OF EMBODIMENTS

Figure 1:
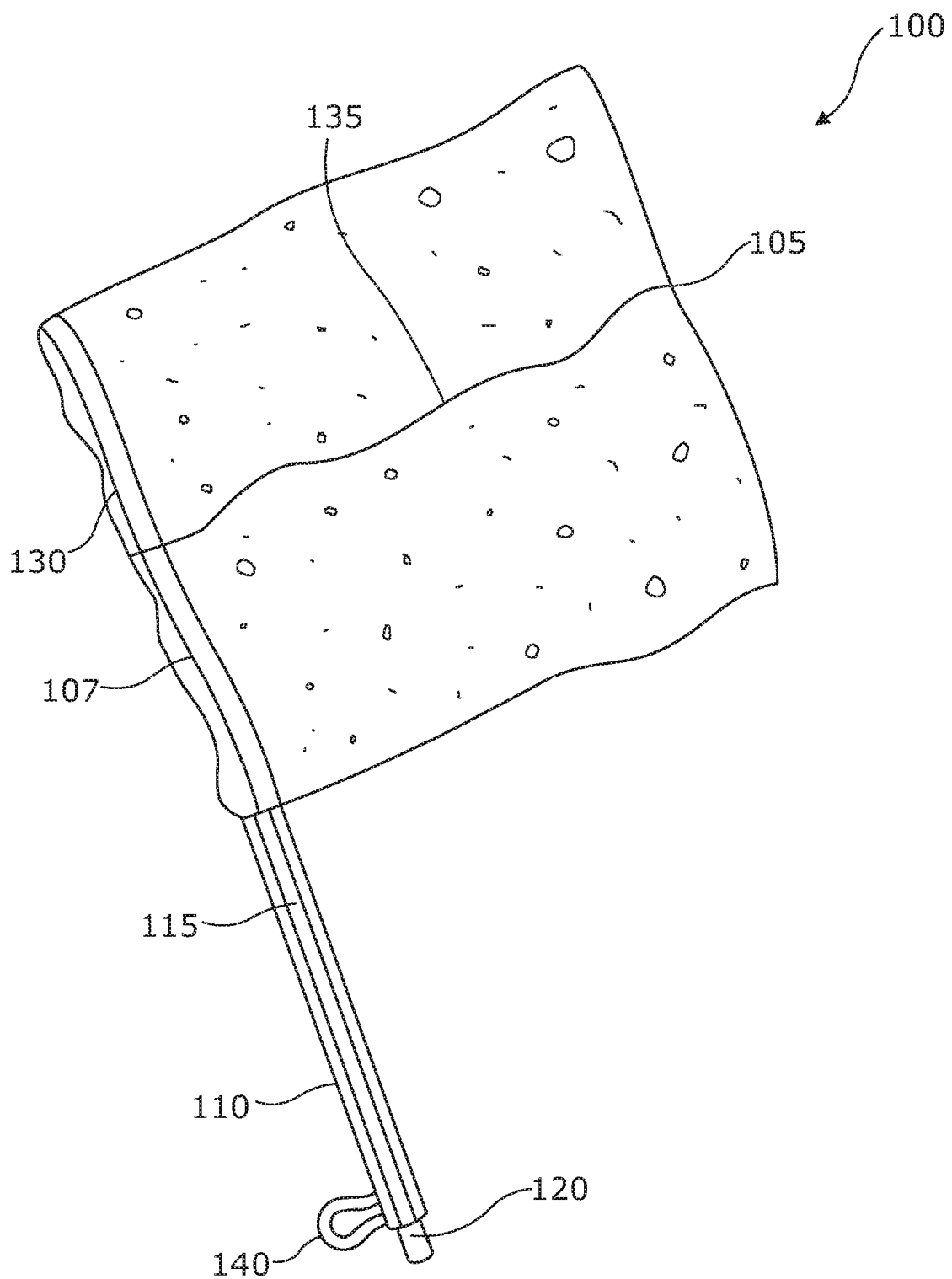
FIG. 1 shows a surgical swab (sponge) for use in a first embodiment of the invention.
Figure 2:
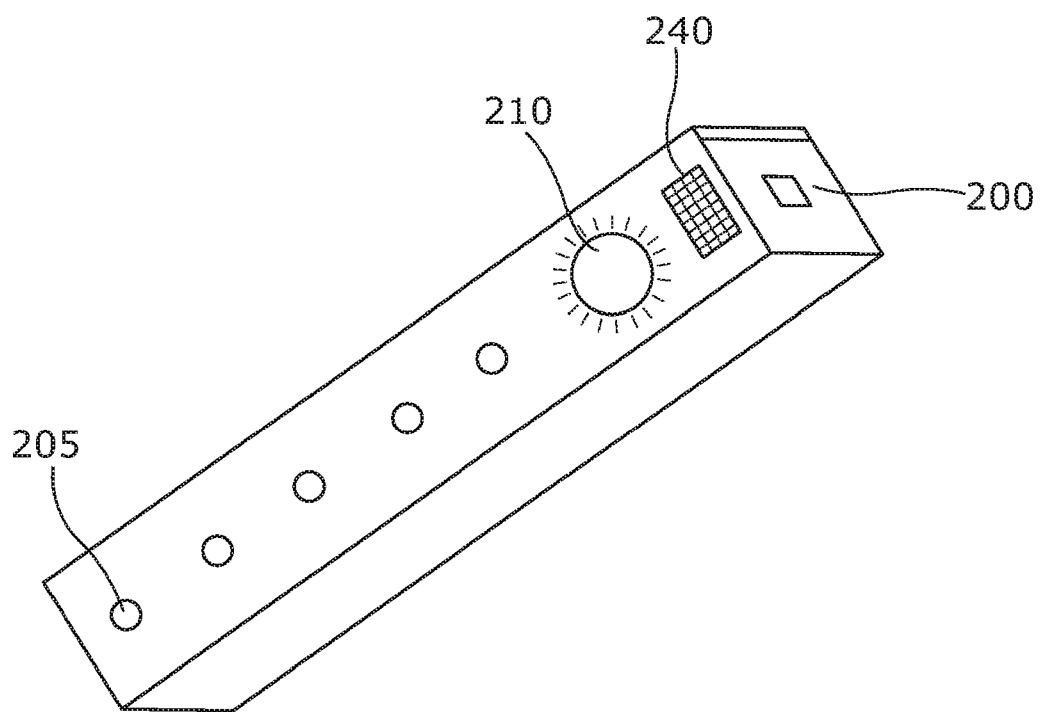
FIG. 2 shows the body of the system of the embodiment of FIG. 1.

FIGS. 1 and 2 of the accompanying drawings show a first embodiment of the invention. Starting with FIG. 2, this shows a body 200 of the form of a cuboid box. The body 200 is provided with five ports 205, each of the form of a standard 3.5 mm jack. It is also provided with a light 210 and a sounder 240.

A surgical swab 100 is shown in FIG. 2; this is an item of surgical equipment sometimes known as a surgical sponge. It comprises a gauze field 105 which is used for absorbing blood and/or other bodily fluids during surgery. One edge 107 of the field 105 is hemmed; from the hemmed edge 105 extends an elongate tail 110 formed as an extension of the hemming. The tail 110 has a 3.5 mm plug 120 at its distal end.

A loop of the tail material 140 is also provided at the distal end of the tail 120; this allows a surgeon to attach a clamp to the loop 140 during surgery for easier location of the swab 100 during surgery. Radio-opaque metallic threads 115, 130 run down the length of the tail 120 and hemmed edge 107 and a further radio-opaque thread 135 runs perpendicular to those threads. These threads 115, 130, 135 aid location of the swab 100 using x-ray techniques.

During surgery, a number of items of surgical equipment such as swab 100 will be required. Using the apparatus of this embodiment of the invention, the presence of five of those items can be tracked; fewer or more items can be tracked by providing fewer or more ports 205. Before the surgery commences, the body will be provided with the plugs 120 of each of the items of surgical equipment engaged in the ports 205 of the body 200. The light 210 will illuminate (potentially green) in order to indicate that all five items are accounted for. Typically, a two-person check would be made of this, and the check recorded.

As the surgery progresses, the items of surgical equipment will be detached from body 200 so that they can be used. As soon as any one of the plugs 120 are disconnected from the respective port 205, the light will indicate (potentially by changing colour, e.g. to red, or by extinguishing) that not all the ports 120 are occupied. The sounder 240 will emit a sound every three minutes to remind those involved with the surgery that not all of the items of surgical equipment have been accounted for.

As the surgery concludes, the surgeon(s) or those assisting them will remove the items of surgical equipment. As they are removed, the plugs 120 are reintroduced into the ports 205. Once all five plugs 120 have been inserted into the five ports 205—thus indicating that all five items of surgical equipment have been removed from the patient—the light 210 will indicate that all five ports are occupied (e.g. by turning green once more) and the regular sound from sounder 240 will cease (and potentially a different, "all-clear" sound will be emitted). Again, this should be a two-person check, which can be recorded.

These indications can therefore indicate that all of the items of surgical equipment have been removed from the patient, and that it is now safe to close up any incisions that have been made into the patient.

Figure 3:
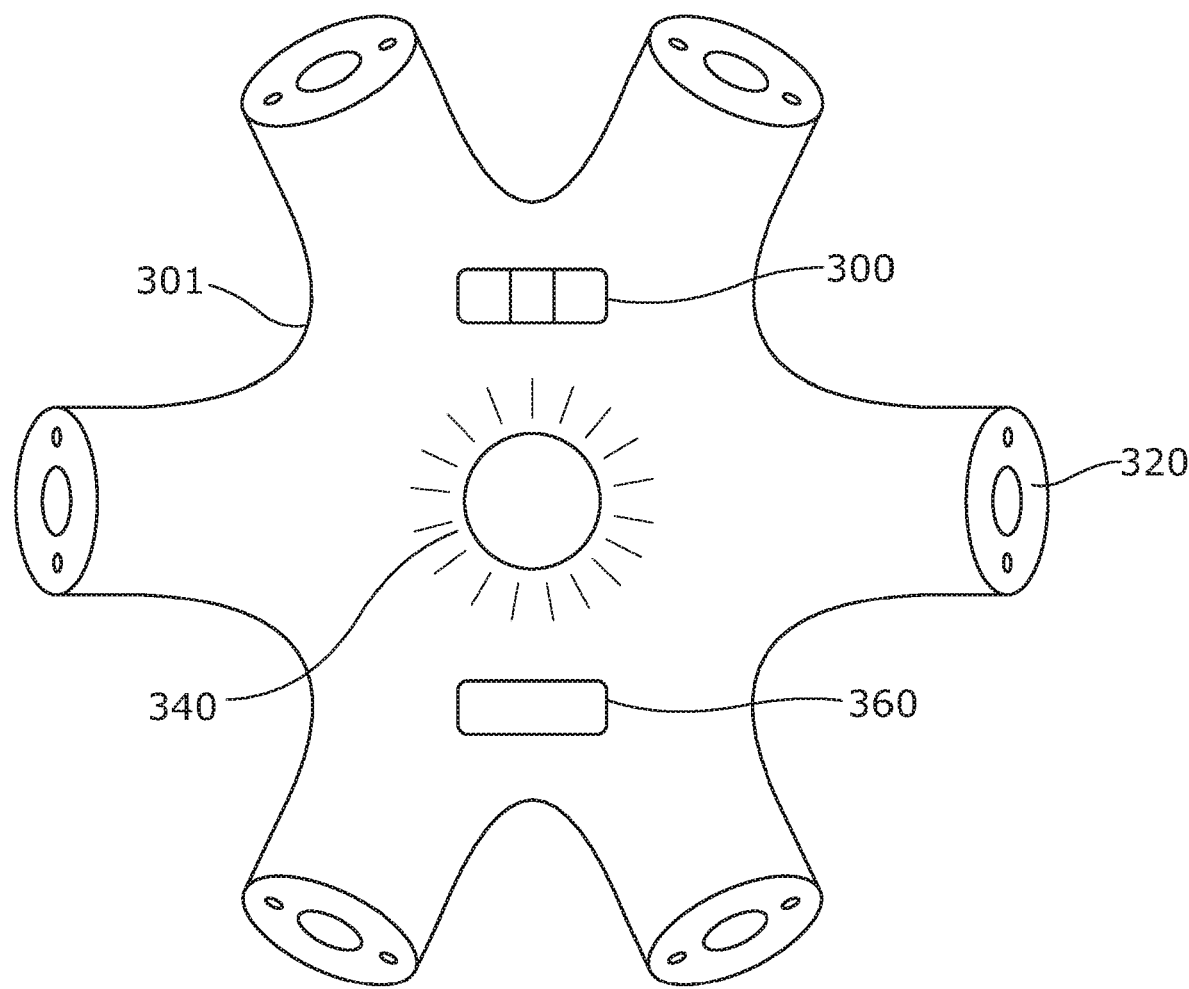
FIG. 3 shows a body in accordance with a second embodiment of the invention.
Figure 4:
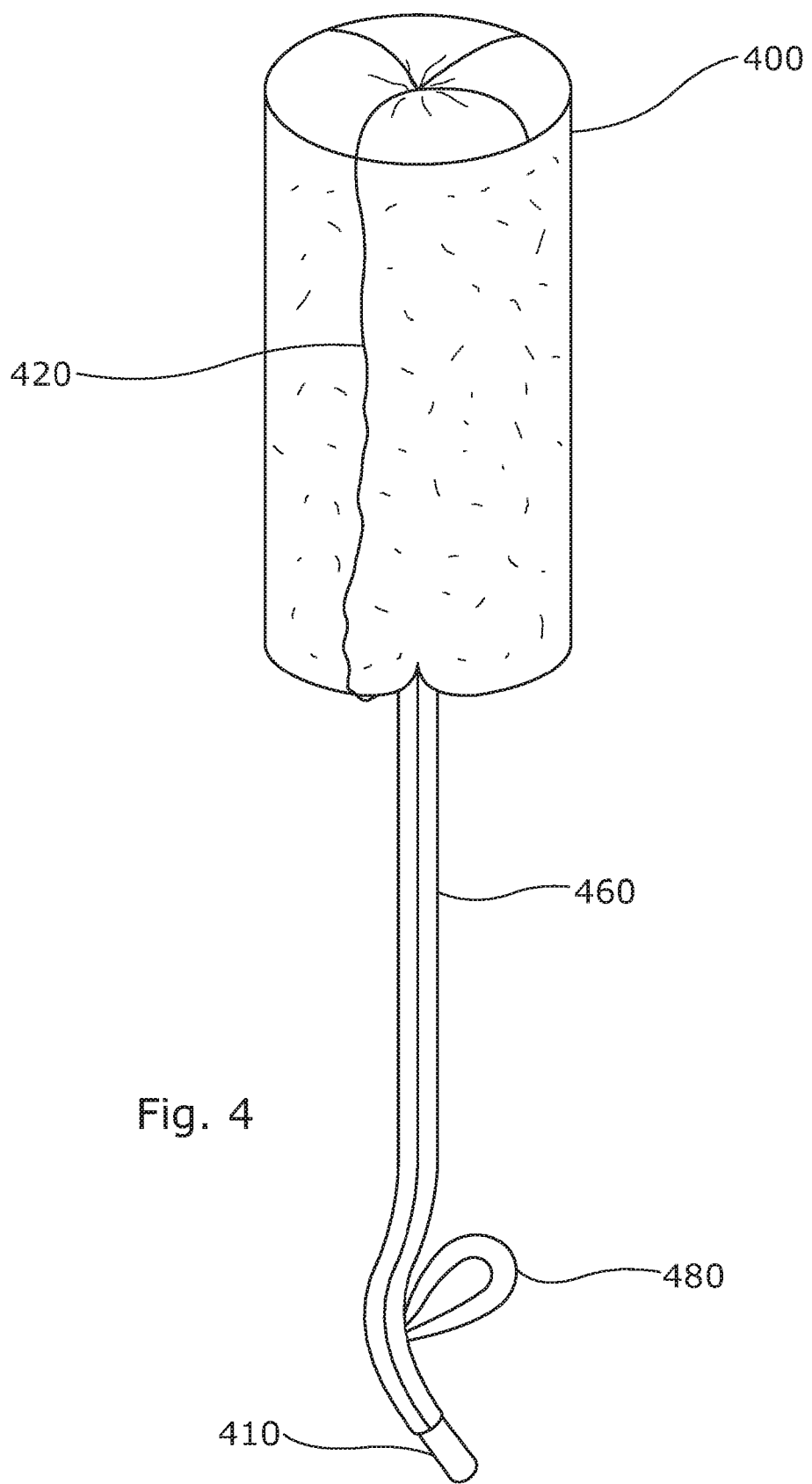
FIG. 4 shows a vaginal tampon for use with the body of FIG. 3.

A second embodiment of the invention is shown in FIGS. 3 to 4 of the accompanying drawings. In this embodiment, the body 301 has a shape with six-fold rotational symmetry, with a jack 320 at the end of each of six arms. At the centre of the body 301, there is provided a light 340 and a sounder 360, which operate as in the first embodiment described above. There is also a power switch 300, which allows for activate or deactivation of the device. Alternatively, the light 340 could be replaced with a mechanical indicator, with a mechanical linkage from each jack 320 coupling the jacks 320 to the mechanical indicator so that the mechanical indicator changes state (e.g. from red to green) when all of the jacks 320 are engaged by the respective engagement members of items of surgical equipment. Given that the body 301 of this embodiment has six ports or jacks 320, it can track six items of surgical equipment. These could include the swab/sponge of FIG. 1, or alternatively the vaginal tampon of FIG. 4 (as used in a birth pack, comprising sufficient swabs and tampons to enable surgical intervention in the human birth process and the aftermath thereof).

Turning now to FIG. 4, this shows a vaginal tampon. It comprises a cotton body 400, which is absorbent to blood and other bodily fluids. It has a tail 460 extending from the body 400. A radio-opaque thread 420 runs the length of the body 400 and down the tail 460. The distal end of the tail 460 is provided with a 3.5 mm plug 410 to match jacks 320. A loop 480 of the tail material is also provided at the distal end of the tail 460 to allow a surgeon to attach a clamp during surgery.

As such, the apparatus of this embodiment of the invention would work in exactly the same manner as that of the first embodiment, save that there are six jacks/ports 320 to fill use, so six items of surgical equipment can be tracked, and that there is a power switch 300 to be switched on at the commencement of use.

Figure 5:
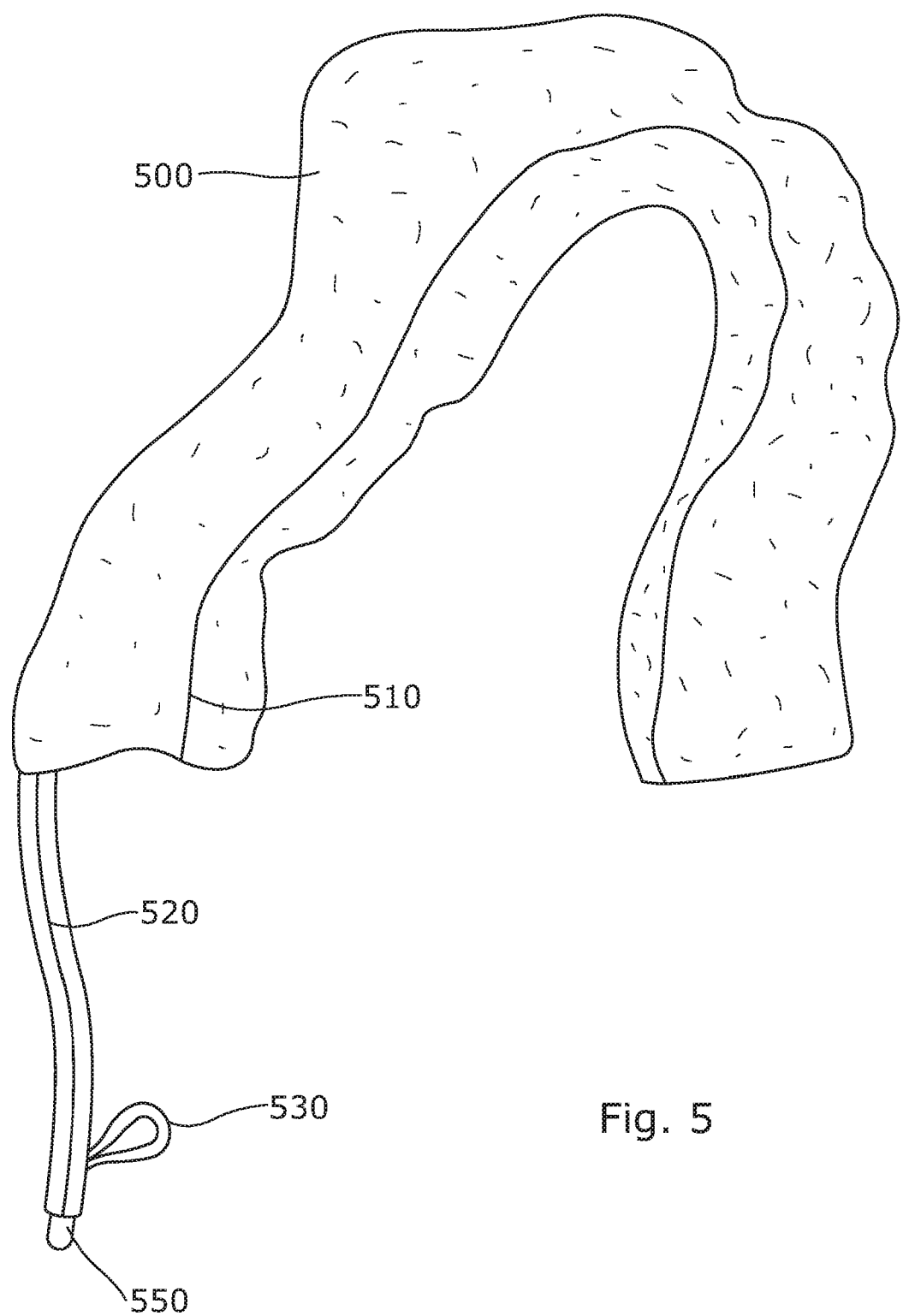
FIG. 5 shows a throat pack for use in a third embodiment of the invention.
Figure 6:
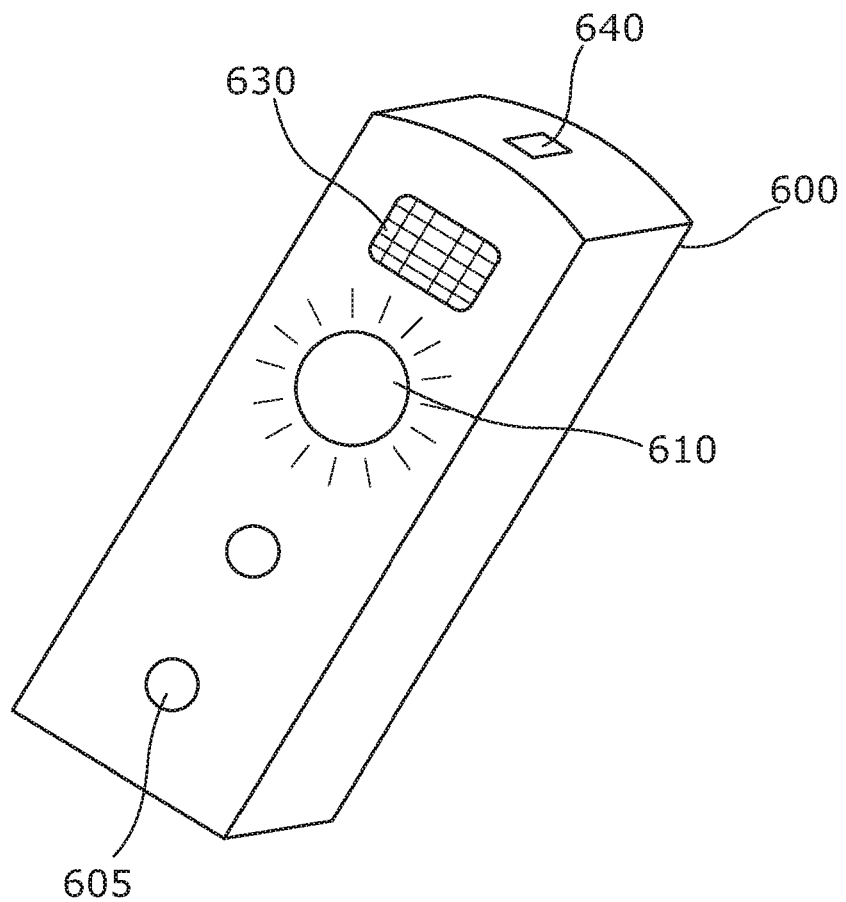
FIG. 6 shows a body for with the throat pack of FIG. 5.

A third embodiment of the invention is shown in FIGS. 5 and 6 of the accompanying drawings. Referring to FIG. 5, this shows a throat pack. This comprises a gauze body 500 which can line a patient's throat. Again, a tail 520 is provided at what would be the upper end of the throat pack in use in a patient. A radio-opaque thread 510 runs the length of the throat pack and into the tail 520. At the distal end of the tail 520 there is a 3.5 mm plug 550 and a loop of material 530 to which a surgeon can attach a clamp.

FIG. 6 shows a body 600 for use in this embodiment. This body has two ports 605 for items of surgical equipment such as the throat pack of FIG. 5. It also has a light 610 and a sounder 630 as in previous embodiments, and a power switch 640 as in the previous embodiment.

As such, the apparatus of this embodiment of the invention would work in exactly the same manner as that of the preceding embodiments, save that there are two jacks/ports 605 to fill use, so two items of surgical equipment can be tracked (e.g. the throat pack of FIG. 5, or any other surgical equipment as described above or otherwise), and that there is a power switch 640 to be switched on at the commencement of use.

In any of the above embodiments, the ports represented by the 3.5 mm jacks and the engagement member represented by the 3.5 mm plugs could be replaced by any other suitable pairing of engaging members.

Likewise, the invention is not limited to the use of swabs/sponges or the like—as long as part of the item of surgical equipment can attach, or can have a tail attached which itself attaches, to the central body, this invention can be used. The device is electromagnetically compatible in the operating theatre environment as it does not transmit any radio frequency or other signals. It does not interfere with any implanted electronic devices such as pacemakers.

Typically, the body and the surgical items would all be made of material that could be easily sterilised, either by use of autoclaves, ethylene oxide gas, gamma radiation, boiling water, disinfectant materials or the like.

Figure 7:
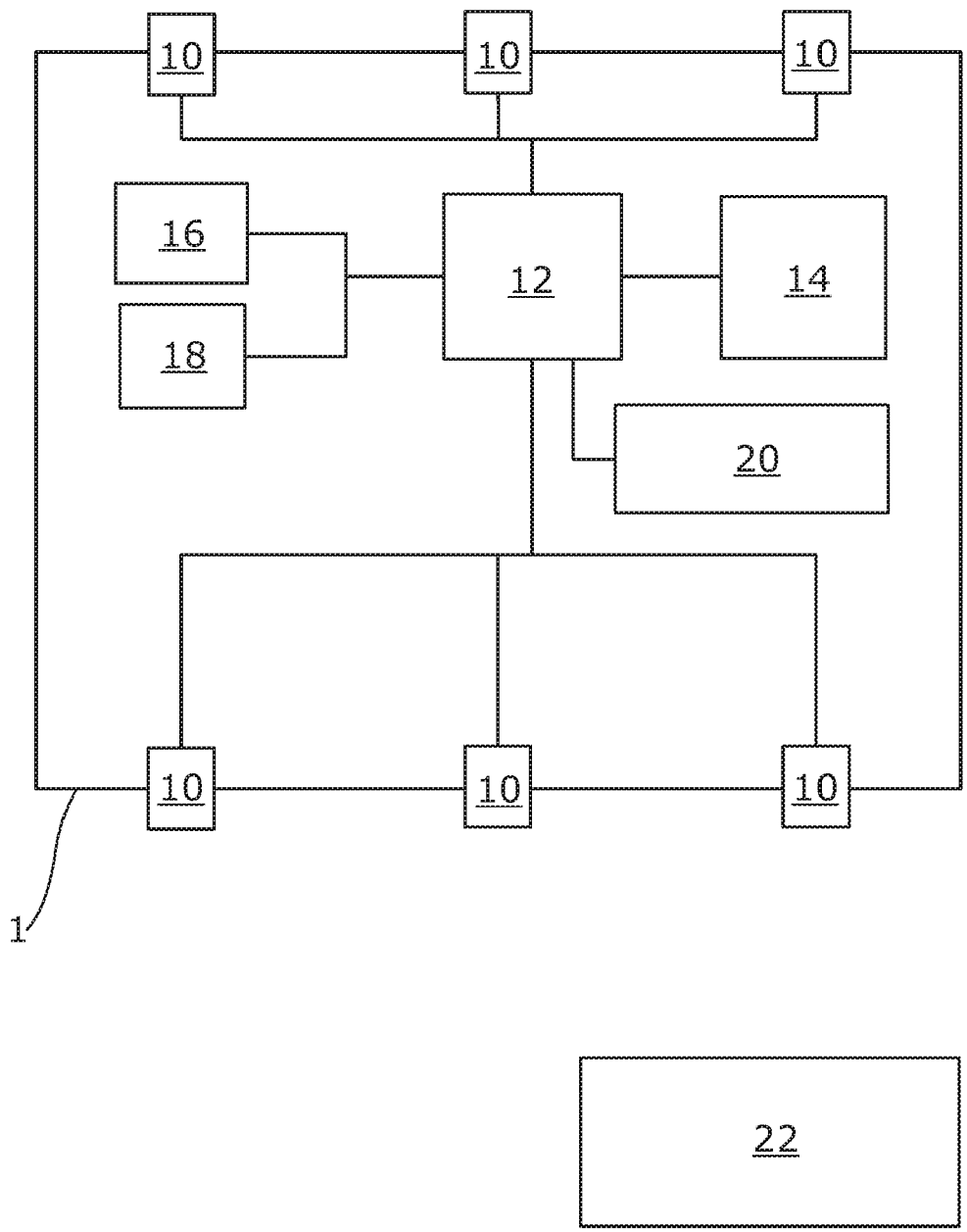
FIG. 7 shows a schematic diagram showing the body of a fourth embodiment of the invention.

A body of a surgical apparatus in accordance with a fourth embodiment of the invention is shown in FIG. 7 of the accompanying drawings. This could be used in any of the preceding embodiments, and serves to explain in more detail the functioning of the body 1.

As in previous embodiments, the body 1 is provided with ports 10; in this case, six ports 10 which could be formed as 3.5 mm jacks as discussed above. The ports are connected to a control circuit 12, which can determine whether the ports 10 have been engaged by corresponding engagement members, such as the plugs on the surgical items shown in FIG. 1, 4 or 5. The control circuit 12 and the other functions of the body 1 are powered by power source 14, such as a battery.

In the simplest embodiment, the control circuit 12 could comprise a simple series circuit connecting a switch at each jack 10 (for example, using the switch commonly found in 3.5 mm to disable a built-in sound source when plugging in headphones). It all of the switches are closed (indicating that the jacks are engaged) then the circuit will complete, indicating all ports are engaged. If any of the switches are open (indicating that at least one jack is not engaged), then there will be an open circuit.

Alternatively, the control circuit 12 could comprise a microprocessor with an input for a switch associated with each jack 10.

The control circuit 12 can control a light 16 and a sounder 18 as discussed above with respect to the first two embodiments.

A transmitter 20 or transceiver circuit can be provided coupled to the control circuit 12, to transmit data concerning the operation of the apparatus and in particular which ports 10 have been engaged to a remote device 22 such as a computer, printer or data logger. This allows for remote auditing and/or viewing of the progress of a surgical operation. The connection would typically be wireless, e.g. Bluetooth (®) or Wi-Fi (®). The data can be printed off at a remote printer, and/or stored in a database.

Figure 8:
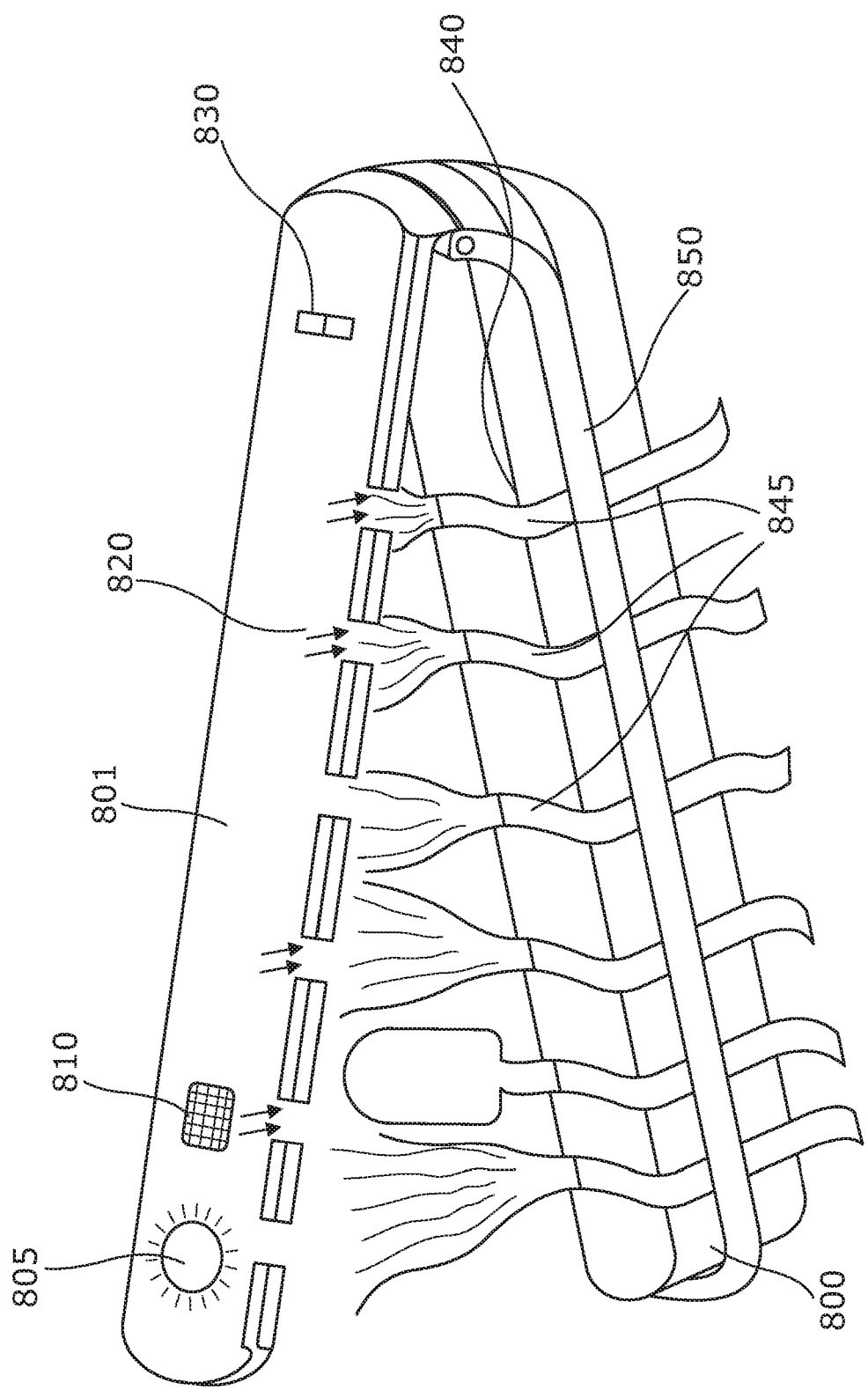
FIG. 8 shows a perspective view of a system in accordance with a fifth embodiment of the invention.

A system in accordance with a fifth embodiment of the invention is shown in FIG. 8 of the accompanying drawings. In this embodiment, rather than the ports being for jacks, the ports are of the form of grooves 845 in body 800 which can be engaged by tails 840. A clasp 850 holds the tails in place. The body 800 is provided with a pivoting lid 801.

If all of the tails 840 are in their respective grooves 845, then the lid 801 can be shut, and a light beam 820 through each of the grooves will be blocked by the respective tails 840. The absence of light at the other side of the grooves 845 can be detected by a suitable light sensor for each groove 845 (not shown) in body 800; if the light beam 820 for each groove 845 is blocked then indicator light 805 can indicate that all tails (and so the items of surgical equipment) are present by, for example, emitting a green light. If any are missing, so that when closed the light beams 820 reach their respective light sensors, the indicator light 820 will indicate that at least one item of surgical equipment is not present (e.g. with a red light). A speaker 810 can provide an additional audible indication of the same information. An on/off switch 830 can control operation of the system.

Figure 9:
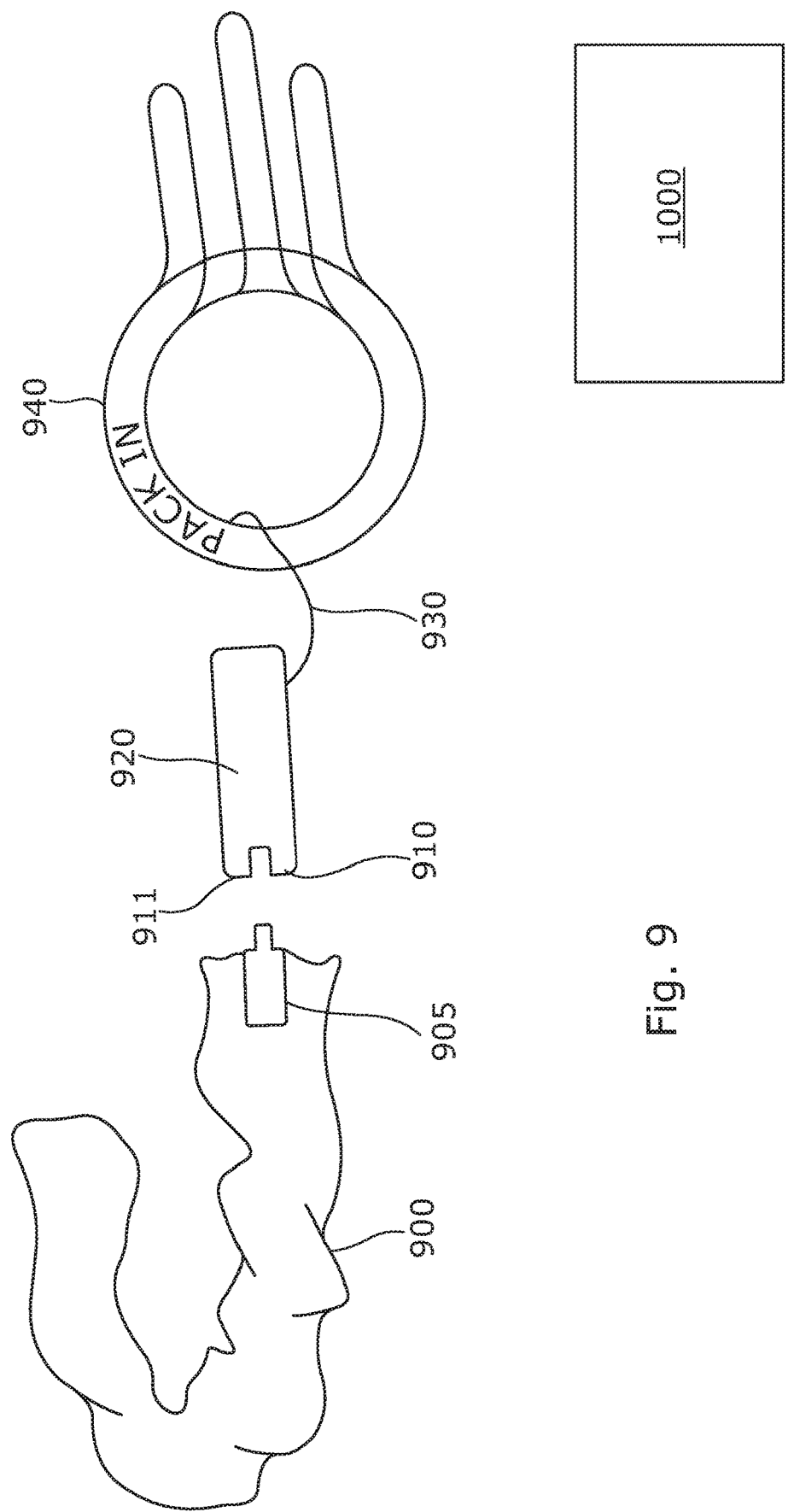
FIG. 9 shows a perspective view of a system in accordance with a sixth embodiment of the invention.

A system in accordance with a sixth embodiment of the invention is shown in FIG. 9 of the accompanying drawings. This comprises a swab 900 formed of a long ribbon of gauze, which can be packed into a vagina or wound where fluid is expected to exude for some time after surgery. As such, whilst the patient can retain the swab 900 after surgery, it is desirable that the swab 900 be removed before the patient leaves hospital.

At present, the presence of such packs is indicated by a patient wristband, with a label "PACK IN". However, patients still occasionally leave hospital with the swab internally.

In order to reduce such occurrences, the swab 900 is provided with an engagement member 905 of the form of male part at an end of the long ribbon of gauze that would extend out of the patient. This engages a port 911 in a body 910. The engagement member may be clipped onto the swab 900.

The body 910 has a light or mechanical indicator 920 which turns from red to green after the engagement member is engaged into the port 911. The body is also attached to a patient wristband 940 as are currently used, via connecting ring 930.

The indicator 920 can also provide an alarm signal to a remote alarm circuit 1000, which would typically be provided at an exit from the word, clinic or hospital (much as similar alarms are provided at the exits from maternity wards to prevent the abduction of babies, or in supermarkets to prevent shoplifting). If the engagement member 905 is not engaged with the port 911 and the patient, wearing the wristband, attempts to walk past the external alarm circuit 1000, an alarm will sound and/or the doors of the ward etc will be locked. This then prevents the patient from leaving the ward etc with the swab 900 still located internally of the patient.

The invention claimed is:

1. A surgical apparatus comprising:
  a body having at least one port; and
  at least one item of surgical equipment configured to be retained inside a patient during surgery and subsequently removed;
  wherein the at least one item of surgical equipment comprises an engagement member arranged to engage the at least one port of the body,
  wherein the surgical apparatus further comprises:
    a control circuit arranged to determine for each of the at least one port whether the engagement member of one of the of the at least one item of surgical equipment is engaged to the respective port; and
    an indicator controlled by the control circuit and arranged to indicate whether the respective engagement member is engaged with the at least one port.

2. The apparatus of claim 1, wherein the indicator comprises a visual indicator including at least one of a light emitting indicator, an audible indicator and a mechanical indicator that is movable between at least two different states depending on whether each respective engagement member is engaged with the respective port.

3. The apparatus of claim 1, wherein the at least one item of surgical equipment comprises at least one item of the following groups:
  surgical swabs/sponges;
  throat packs; and
  surgical vaginal tampons.

4. The apparatus of claim 1, wherein the at least one item of surgical equipment comprises an elongate tail.

5. The apparatus of claim 4, wherein the elongate tail carries the engagement member at one end and is connected to a body of the at least one item at another end.

6. The apparatus of claim 4, wherein the tail includes a loop adjacent to the engagement member.

7. The apparatus of claim 1, wherein the at least one port comprises a socket configured to receive at least one of the engagement members.

8. The apparatus of claim 1, wherein the at least one port comprises a groove configured to receive the engagement member.

9. The apparatus of claim 8, wherein the engagement member comprises the tail of the at least one item of surgical equipment.

10. The apparatus of claim 8, wherein the control circuit comprises a light source and a light sensor for each groove, wherein the control circuit is arranged to determine that the at least one item of surgical equipment is engaged in the port if light from the light source is blocked by the engagement member and does not reach the light sensor.

11. The apparatus of claim 1, wherein the control circuit comprises transmission means arranged to transmit a status of the engagement of the engagement members in the at least one port to a remote location.

12. The apparatus of claim 1, in which the body has a plurality of ports, and there are a plurality of items of surgical equipment.

13. The apparatus of claim 1, wherein the body is configured to be worn on the patient's body.

14. The apparatus of claim 1, wherein the body or the engagement member comprises a signalling circuit configured to signal to an external alarm circuit that the at least one item of surgical equipment is still within the patient.

15. The apparatus of claim 14, wherein the signalling circuit is deactivated when the engagement member engages the at least one port of the body.

16. The apparatus of claim 14, further comprising the external alarm circuit.

17. A surgical apparatus comprising:
  a body having a plurality of ports; and
  a plurality of items of surgical equipment, each item being configured to be retained inside a patient during surgery and subsequently removed;
  wherein each of the plurality of items of surgical equipment comprises an engagement member arranged to engage one port of the plurality of ports, and wherein the apparatus further comprises:
- a control circuit arranged to determine for each port whether the engagement member of one of the plurality of items of surgical equipment is engaged to the respective port; and
- an indicator controlled by the control circuit and arranged to indicate whether the engagement members are engaged with the plurality of ports.

18. A method of surgery using the apparatus of claim 17, comprising:
- providing each item of surgical equipment with the engagement member of each item connected to one of the plurality of ports of the body;
- detaching the engagement member(s) from the port(s) in order to use the item(s) in surgery;
- using the item(s) of surgical equipment in surgery on a patient;
- after the usage of each item of surgical equipment, engaging the engagement member to a respective port of the plurality of ports of the body; and
- before the surgery has finished, checking that the indicator indicates that each engagement member has been engaged with a respective port of the plurality of ports.

19. The apparatus of claim 1, wherein the control unit further comprises a mechanical mechanism configured to move the indicator.

* * * * *